(12) United States Patent
Zarembo et al.

(10) Patent No.: US 8,055,354 B2
(45) Date of Patent: *Nov. 8, 2011

(54) INTERCONNECTIONS OF IMPLANTABLE LEAD CONDUCTORS AND ELECTRODES AND REINFORCEMENT THEREFOR

(75) Inventors: Paul E. Zarembo, Vadnais Heights, MN (US); Mohan Krishnan, Shoreview, MN (US); David Durand, Osceola, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 247 days.

This patent is subject to a terminal disclaimer.

(21) Appl. No.: 12/467,978

(22) Filed: May 18, 2009

(65) Prior Publication Data

US 2009/0222074 A1  Sep. 3, 2009

Related U.S. Application Data

(62) Division of application No. 11/305,925, filed on Dec. 19, 2005, now Pat. No. 7,546,165.

(51) Int. Cl.
*A61N 1/05* (2006.01)
(52) U.S. Cl. ....................................... 607/122
(58) Field of Classification Search .................... 607/37, 607/122
See application file for complete search history.

(56) References Cited

U.S. PATENT DOCUMENTS

| | | | |
|---|---|---|---|
| 3,474,791 A | 10/1969 | Bentov | |
| 4,214,804 A | 7/1980 | Little | |
| 4,280,511 A | 7/1981 | O'Neill | |
| 4,328,812 A | 5/1982 | Ufford et al. | |
| 4,379,462 A | 4/1983 | Borkan et al. | |
| 4,413,636 A | 11/1983 | Jasso | |
| 4,466,690 A | 8/1984 | Osypka | |
| 4,484,586 A | 11/1984 | McMickle et al. | |
| 4,538,623 A | 9/1985 | Proctor et al. | |

(Continued)

FOREIGN PATENT DOCUMENTS

EP   0778048 A1   6/1997

(Continued)

OTHER PUBLICATIONS

"International Search Report for corresponding PCT Application PCT/US2006/037527", 6 pgs.

(Continued)

*Primary Examiner* — Carl H Layno
*Assistant Examiner* — Luther Behringer
(74) *Attorney, Agent, or Firm* — Faegre & Benson LLP

(57) ABSTRACT

An implantable lead comprises a lead body extending from a lead proximal end portion to a lead distal end portion. The lead body includes one or more longitudinally extending lumens. A conductor is received in, and extends along, a lumen. In varying examples, the implantable lead further comprises a tubular electrode co-axial with, and overlying portions of, the lead body. In one example, a lumen wall is sized and shaped to urge an electrically conductive interposer coupled with the conductor toward an inner surface of the electrode. In another example, a ring member is disposed within a lumen and the conductor is drawn and coupled thereto. In yet another example, an electrically conductive connector couples a first and a second conductor via grooves or threads. In a further example, an axial support member couples a distal end electrode and the lead body. Methods associated with the foregoing are also discussed.

22 Claims, 13 Drawing Sheets

U.S. PATENT DOCUMENTS

| | | |
|---|---|---|
| 4,573,481 A | 3/1986 | Bullara |
| 4,592,372 A | 6/1986 | Beranek |
| 4,628,934 A | 12/1986 | Pohndorf et al. |
| 4,643,202 A | 2/1987 | Roche |
| 4,711,027 A | 12/1987 | Harris |
| 4,721,115 A | 1/1988 | Owens |
| 4,860,446 A | 8/1989 | Lessar et al. |
| 4,922,607 A | 5/1990 | Doan et al. |
| 4,934,049 A | 6/1990 | Kiekhafer et al. |
| 5,007,435 A | 4/1991 | Doan et al. |
| 5,014,720 A | 5/1991 | Barcel et al. |
| 5,016,808 A | 5/1991 | Heil, Jr. et al. |
| 5,040,544 A | 8/1991 | Lessar et al. |
| 5,076,270 A | 12/1991 | Stutz, Jr. |
| 5,115,818 A | 5/1992 | Holleman et al. |
| 5,170,802 A | 12/1992 | Mehra |
| 5,217,027 A | 6/1993 | Hermens |
| 5,224,491 A | 7/1993 | Mehra |
| 5,231,996 A | 8/1993 | Bardy et al. |
| 5,251,643 A | 10/1993 | Osypka |
| 5,303,704 A | 4/1994 | Molacek et al. |
| 5,324,321 A | 6/1994 | Pohndorf et al. |
| 5,330,522 A | 7/1994 | Kreyenhagen |
| 5,347,708 A | 9/1994 | Bischoff et al. |
| 5,350,419 A | 9/1994 | Bendel et al. |
| 5,387,233 A | 2/1995 | Alferness et al. |
| 5,417,208 A | 5/1995 | Winkler |
| 5,423,865 A | 6/1995 | Bowald et al. |
| 5,431,683 A | 7/1995 | Bowald et al. |
| 5,449,381 A | 9/1995 | Imran |
| 5,458,629 A | 10/1995 | Baudino et al. |
| 5,476,498 A | 12/1995 | Ayers |
| 5,483,022 A | 1/1996 | Mar |
| 5,487,757 A | 1/1996 | Truckai et al. |
| 5,522,872 A * | 6/1996 | Hoff ............................... 607/119 |
| 5,549,642 A | 8/1996 | Min et al. |
| 5,649,974 A | 7/1997 | Nelson et al. |
| 5,676,694 A | 10/1997 | Boser et al. |
| 5,725,566 A | 3/1998 | Pioger et al. |
| 5,746,616 A * | 5/1998 | Mar ............................... 439/245 |
| 5,845,396 A | 12/1998 | Altman et al. |
| 5,871,531 A | 2/1999 | Struble |
| 5,910,129 A | 6/1999 | Koblish et al. |
| 5,935,159 A | 8/1999 | Cross, Jr. et al. |
| 5,954,759 A | 9/1999 | Swoyer et al. |
| 5,957,970 A | 9/1999 | Shoberg et al. |
| 6,018,684 A * | 1/2000 | Bartig et al. .................. 607/122 |
| 6,055,457 A | 4/2000 | Bonner |
| 6,083,216 A | 7/2000 | Fischer, Sr. |
| 6,129,750 A | 10/2000 | Tockman et al. |
| 6,144,870 A | 11/2000 | Griffin, III |
| 6,161,029 A | 12/2000 | Spreigl et al. |
| 6,181,971 B1 | 1/2001 | Doan |
| 6,256,541 B1 | 7/2001 | Heil et al. |
| 6,256,542 B1 | 7/2001 | Marshall et al. |
| 6,289,251 B1 | 9/2001 | Huepenbecker et al. |
| 6,301,507 B1 | 10/2001 | Bakels et al. |
| 6,321,123 B1 | 11/2001 | Morris et al. |
| 6,363,288 B1 | 3/2002 | Bush et al. |
| 6,366,820 B1 | 4/2002 | Doan et al. |
| 6,374,476 B1 | 4/2002 | Ponzi et al. |
| 6,400,992 B1 | 6/2002 | Borgersen et al. |
| 6,430,449 B1 | 8/2002 | Hsu et al. |
| 6,434,430 B2 | 8/2002 | Borgersen et al. |
| 6,466,820 B1 | 10/2002 | Juran et al. |
| 6,477,427 B1 | 11/2002 | Stolz et al. |
| 6,501,990 B1 | 12/2002 | Sundberg et al. |
| 6,501,991 B1 | 12/2002 | Honeck et al. |
| 6,505,081 B1 | 1/2003 | Das |
| 6,505,401 B1 | 1/2003 | Doan |
| 6,516,232 B2 | 2/2003 | Skinner |
| 6,556,873 B1 | 4/2003 | Smits |
| 6,567,704 B2 | 5/2003 | Sundquist et al. |
| 6,584,362 B1 | 6/2003 | Scheiner et al. |
| 6,643,550 B2 | 11/2003 | Westlund et al. |
| 6,650,945 B2 | 11/2003 | Helland et al. |
| 6,721,598 B1 | 4/2004 | Helland et al. |
| 6,757,970 B1 | 7/2004 | Kuzma et al. |
| 6,785,576 B2 | 8/2004 | Verness |
| 6,801,809 B2 | 10/2004 | Laske et al. |
| 6,843,870 B1 | 1/2005 | Bluger |
| 6,856,822 B2 | 2/2005 | Larsson |
| 6,871,085 B2 | 3/2005 | Sommer |
| 6,882,886 B1 | 4/2005 | Witte et al. |
| 6,895,277 B2 | 5/2005 | Westlund et al. |
| 6,912,423 B2 * | 6/2005 | Ley et al. .......................... 607/37 |
| 7,212,868 B2 * | 5/2007 | McAuliffe et al. ........... 607/116 |
| 7,546,165 B2 | 6/2009 | Zarembo et al. |
| 2002/0082651 A1 | 6/2002 | Stahmann et al. |
| 2002/0107551 A1 | 8/2002 | Stahmann et al. |
| 2002/0147484 A1 | 10/2002 | Dahl et al. |
| 2003/0074031 A1 | 4/2003 | Ley et al. |
| 2003/0199950 A1 | 10/2003 | Stolz et al. |
| 2003/0208119 A1 | 11/2003 | Crowley |
| 2004/0014355 A1 | 1/2004 | Osypka et al. |
| 2004/0064173 A1 | 4/2004 | Hine et al. |
| 2004/0064174 A1 | 4/2004 | Belden |
| 2004/0215299 A1 | 10/2004 | Zhao et al. |
| 2004/0230279 A1 | 11/2004 | Cates et al. |
| 2004/0230280 A1 | 11/2004 | Cates et al. |
| 2004/0230281 A1 | 11/2004 | Heil et al. |
| 2004/0230282 A1 | 11/2004 | Cates et al. |
| 2004/0243210 A1 | 12/2004 | Morgan et al. |
| 2004/0260374 A1 | 12/2004 | Zhang et al. |
| 2004/0260375 A1 | 12/2004 | Zhang et al. |
| 2005/0004642 A1 | 1/2005 | Shoberg |
| 2005/0010095 A1 | 1/2005 | Stewart et al. |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0060013 A1 | 3/2005 | van den Nieuwenhof et al. |
| 2005/0228469 A1 | 10/2005 | Zarembo et al. |
| 2007/0142890 A1 | 6/2007 | Zarembo et al. |

FOREIGN PATENT DOCUMENTS

| | | |
|---|---|---|
| FR | 2508716 | 12/1982 |
| WO | WO-2007078360 A2 | 7/2007 |

OTHER PUBLICATIONS

"Partial Search Report for PCT Application No. PCT/2006/037527", (Mar. 13, 2007), 5.

"Written Opinion of the International Searching Authority for corresponding PCT Application No. PCT/US2006/037527", (Jul. 31, 2007), 11 pgs.

Hansen, David J, "Multi-Site Lead/System Using a Multi-Pole Connection and Methods Therefor", U.S. Appl. No. 11/230,989, filed Sep. 20, 2005, 55 Pages.

Zarembo, Paul E, et al., "Device on Lead to Prevent Perforation and/or Fixate Lead", U.S. Appl. No. 11/215,786, Date Mailed Aug. 30, 2005, 43 Pages.

"U.S. Appl. No. 11/305,925, Restriction Requirement mailed Jul. 16, 2008", 7 pgs.

"U.S. Appl. No. 11/305,925, Notice of Allowance mailed Jan. 27, 2009", 7 pgs.

"U.S. Appl. No. 11/305,925, Response filed Nov. 26, 2008 to Non-Final Office Action mailed Sep. 22, 2008", 18 pgs.

"U.S. Appl. No. 11/305,925, Response filed Aug. 18, 2008 to Restriction Requirement mailed Jul. 16, 2008", 8 pgs.

"U.S. Appl. No. 11/305,925, Non-Final Office Action mailed Sep. 22, 2008", 10 pgs.

"European Application Serial No. 06815485.5, Communication mailed Jul. 28, 2008", 2 pgs.

"European Application Serial No. 06815485.5, Office Action mailed Jun. 24, 2009", 4 pgs.

"European Application Serial No. 06815485.5, Response filed Aug. 22, 2008 to Communication mailed Jul. 28, 2008", 14 pgs.

* cited by examiner

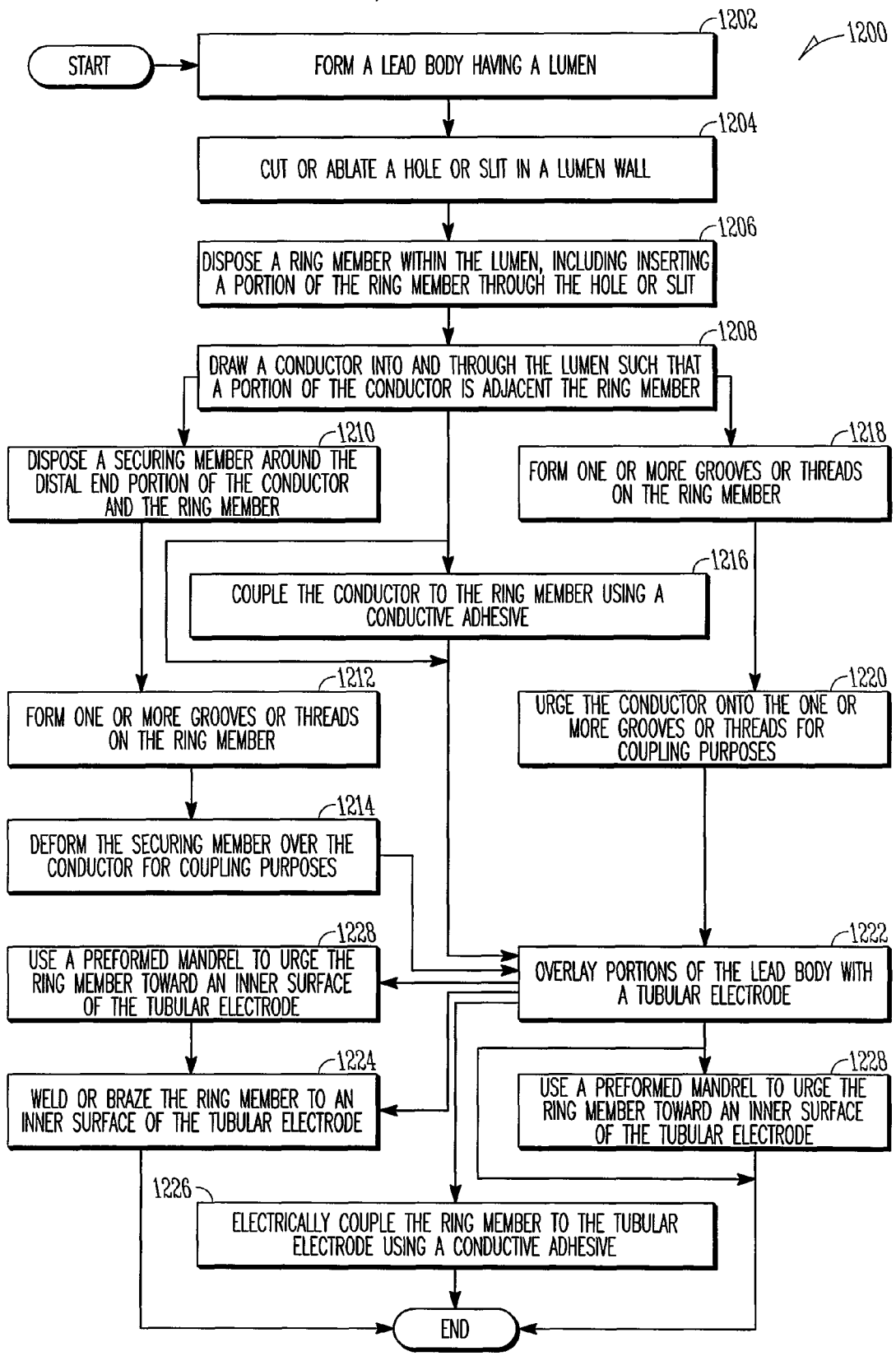

INTERCONNECTIONS OF IMPLANTABLE LEAD CONDUCTORS AND ELECTRODES AND REINFORCEMENT THEREFOR

CROSS-REFERENCE TO RELATED APPLICATIONS

This application is a divisional of U.S. patent application Ser. No. 11/305,925, filed on Dec. 19, 2005, now issued as U.S. Pat. No. 7,546,165, the specification of which is incorporated herein in its entirety by reference.

TECHNICAL FIELD

This patent document pertains generally to implantable leads for linking implantable medical devices with selected body tissue to be sensed or stimulated by such devices. More particularly, but not by way of limitation, this patent document pertains to interconnections of implantable lead conductors and electrodes and reinforcement therefor.

BACKGROUND

Implantable leads represent the electrical link between an implantable medical device (often referred to simply as "IMD") and a subject's cardiac or other tissue, which is to be sensed or stimulated. An implantable lead may include a single or multiple conductors that are connected to an electrode or an electrode assembly at a lead intermediate portion or a lead distal end portion. A connector is included at a lead proximal end portion to form an electrical connection (via the conductor(s)) between the electrode or electrode assembly and the IMD.

Over the years, a large number of different mechanisms and methods for interconnecting conductors and electrodes have been proposed. It is desirable that such connections between the conductor and the electrode provide a highly reliable electrical connection, with good mechanical properties including high tensile strength. It is also desirable that such connections allow for the lead assembly itself to retain a high degree of tensile strength through the area of the electrode. This is because cardiac (and other) leads undergo considerable stresses due to repetitive flexing caused by, for example, the motion of a beating heart and forces applied to the lead during an implantation, repositioning, or lead extraction procedure.

Typically, conductors in commercially marketed pacing and defibrillation leads have taken the form of single or multi-filar wire coils. Recently, there has been a high level of interest in designing leads having lead bodies with a reduced size (i.e., lead body diameter) or additional electrodes. One way to reduce to lead body size is to employ stranded wire conductors such as cables in lieu of coiled wire conductors. However, such stranded wire conductors present new challenges not faced by the use of coiled wire conductors. As one example, it has been a great challenge to electrically and reliably connect a small multi-strand conductor cable (often times having a cable outer diameter on the order of thousandths of an inch) to a ring electrode or a multi-filar shock coil electrode. Being of such small size, the connection is a very difficult one to make and fragile, if made incorrectly.

With respect to single or multi-filar wire coiled conductors, when such conductors are used to electrically connect a distal (tip) electrode to the IMD, portions of the distal electrode typically are polymer bonded (e.g., via an adhesive) to provide additional axial strength to the electrode. However, even with such additional polymer-provided strength, the distal electrode/lead body connection may still fall short of the axial strength necessary to resist permanent deformation or in order to pass industry standards (e.g., CEN/CENELEC 45502-2-1, §23.3).

SUMMARY

An implantable lead comprises a lead body extending from a lead proximal end portion to a lead distal end portion, with a lead intermediate portion therebetween. The lead body includes one or more longitudinally extending lumens. A conductor is received in, and extends along, a first lumen. An electrically conductive interposer, coupled with the conductor, is also received, at least in part, in the first lumen. The implantable lead further comprises a tubular electrode that is co-axial with, and overlays portions of, the leady body. In varying examples, a portion of a first lumen wall compressively urges the interposer toward an inner surface of the tubular electrode.

Another implantable lead comprises a lead body extending from a lead proximal end portion to a lead distal end portion. The lead body includes an internal longitudinally extending lumen. A ring member is disposed within the lumen such that a portion of the ring member extends through a hole or slit (collectively termed "aperture") in a lumen wall. A conductor is received in, and extends along, the lumen. A distal end portion of the conductor is drawn adjacent to an outer surface of the ring member and electrically coupled thereto. The implantable lead further comprises a tubular electrode that is co-axial with, and overlays portions of, the lead body. The tubular electrode is electrically coupled with the conductor via the ring member.

Yet another implantable lead comprises a lead body extending from a lead proximal end portion to a lead distal end portion, with at least one of a lumen or a slit therein. The lead comprises a first and a second conductor along with an electrically conductive connector. The electrically conductive connector includes a first end portion coupled with the first conductor and a second end portion coupled with the second conductor. The electrically conductive connector is received in the lumen or slit of the lead body. The lead further comprises a securing member disposed and deformed around a portion of one or both of the first conductor of the second conductor.

A further implantable lead comprises a lead body extending from a lead proximal end portion to a lead distal end portion, with a lead intermediate portion therebetween. The lead body includes at least a first and a second internal longitudinally extending lumens. A conductor is received in, and extends along, the first lumen and electrically couples to a distal electrode at the lead distal end portion. An axial support member is received in the second lumen and extends from an axial support member proximal end portion to an axial support member distal end portion. A first retaining member engaged with the lead body is coupled with the axial support member proximal end, while a second retaining member engaged with the distal electrode is coupled with the axial support member distal end.

The leads and methods described herein provide numerous advantages over conventional lead designs including secure electrical and mechanical connection between a conductor, such as a small multi-strand conductor cable, and an electrode (e.g., a ring electrode or a multi-filar shock coil electrode). In addition, the leads and methods provide axial reinforcement between a distal electrode and a lead body. Furthermore, the leads and methods allow for the creation of a small-sized lead (e.g., sub-5 French), which advantageously provides for easier and deeper lead delivery and lower sensing/stimulating thresholds. In one such example, the present leads and methods provide a small-sized lead with multiple conductors and electrodes. Multiple conductors and electrodes allow for electrode switching to prevent extra bodily tissue stimulation and optimize a variety of other sensing/stimulating related parameters (e.g., parameters relating to the selection of electrodes/vectors with the best thresholds, or optimizing hemodynamics) as further described in Hansen, et al., U.S. patent application Ser. No. 11/230,989, titled "MULTI-SITE LEAD/SYSTEM USING A MULTI-POLE CONNECTION AND METHODS THEREFOR," filed Sep. 20, 2005, which is hereby incorporated by reference in its entirety.

Several other advantages are also made possible by the present leads and methods. In some examples, the leads and methods reduce or eliminate the reliance on adhesives to couple a conductor to an electrode. Advantageously, by reducing or eliminating reliance on adhesives, manufacturing efficiency can be increased (e.g., may not need to wait for adhesives to cure), and conductor/electrode joint failure caused by adhesive bond strength decreasing over time (e.g., due to reactions with bodily fluids or improper adhesive preparation) can be reduced or eliminated. These and other examples, aspects, advantages, and features of the leads and methods described herein will be set forth in part in the detailed description, which follows, and in part will become apparent to those skilled in the art by reference to the following description of the present leads and methods, and drawings or by practice of the same.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in this patent document.

FIG. 12 is a flow diagram illustrating another method of manufacturing an implantable lead, as constructed in accordance with at least one embodiment.

DETAILED DESCRIPTION

The following detailed description includes references to the accompanying drawings, which form a part of the detailed description. The drawings show, by way of illustration, specific embodiments in which the present leads and methods may be practiced. These embodiments, which are also referred to herein as "examples," are described in enough detail to enable those skilled in the art to practice the present leads and methods. The embodiments may be combined or varied, other embodiments may be utilized or structural or logical changes may be made without departing from the scope of the present leads and methods. It is also to be understood that the various embodiments of the present leads and methods, although different, are not necessarily mutually exclusive. For example, a particular feature, structure or characteristic described in one embodiment may be included within other embodiments. The following detailed description is, therefore, not to be taken in a limiting sense, and the scope of the present leads and methods are defined by the appended claims and their equivalents.

In this document the terms "a" or "an" are used to include one or more than one; the term "or" is used to refer to a nonexclusive or, unless otherwise indicated; and the term "subject" is used synonymously with the term "patient."

Leads and methods discussed herein advantageously provide for secure electrical and mechanical connections between a conductor and an electrode or a conductor and another conductor, while further providing a small lead body diameter. In one example, a lead includes a (cable) conductor/electrode connection design using the compressive or elastic nature of a (polymer) lead body in conjunction with an appropriately (larger) sized electrically conductive interposer (e.g., metallic tube). In another example, a lead includes a (coil) conductor/electrode connection design using a ring member. In yet another example, a lead includes a conductor/conductor connection design using an electrically conductive connector couplable with a first conductor on a first end and couplable with a second conductor on a second end. In a further example, a lead includes an axial support member to reinforce a connection between a distal electrode and (a portion of) the lead body.

Figure 1:
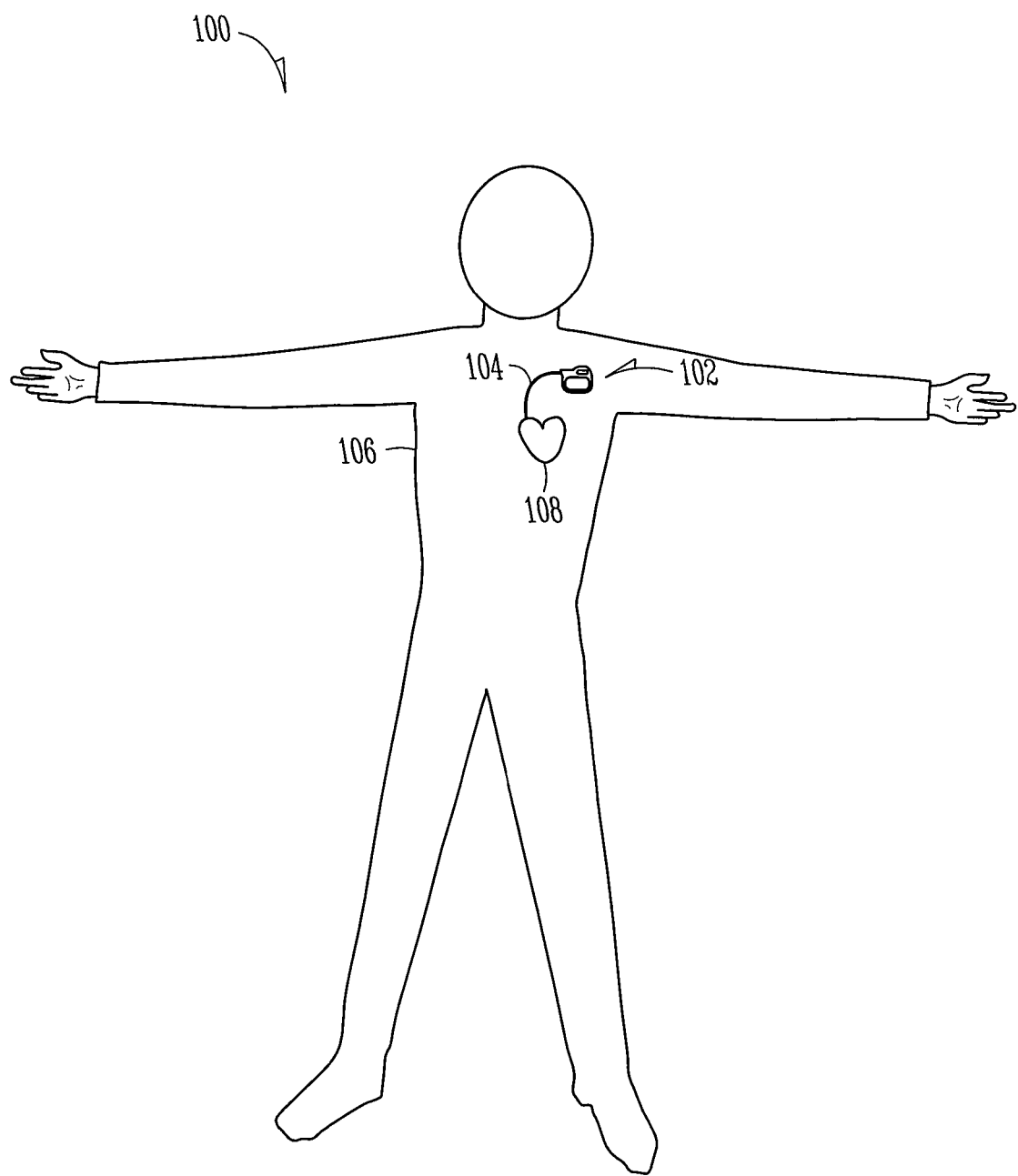
FIG. 1 is a schematic view illustrating an implantable lead system and an environment in which the lead system may be used, as constructed in accordance with at least one embodiment.

Turning now to the drawings, and initially to FIG. 1, which illustrates a lead system 100 and an environment 106 (e.g., subcutaneous pocket made in the wall of a subject's chest, abdomen, or elsewhere) in which lead system 100 may be used. In varying examples, lead system 100 may be used for delivering or receiving electrical pulses or signals to stimulate or sense a heart 108 of a subject. As shown in FIG. 1, lead system 100 includes an implantable medical device (referred to as "IMD") 102 and an implantable lead 104. IMD 102 includes a source of power as well as an electronic circuitry portion. In this example, IMD 102 is a battery-powered device that senses intrinsic signals of heart 108 and generates a series of timed electrical discharges. IMD 102 generically represents, but is not limited to, cardiac rhythm management devices (referred to as "CRM devices") such as pacers, cardioverters, biventricular/cardiac resynchronization paces, defibrillators, and sensing instruments.

Figure 2A:
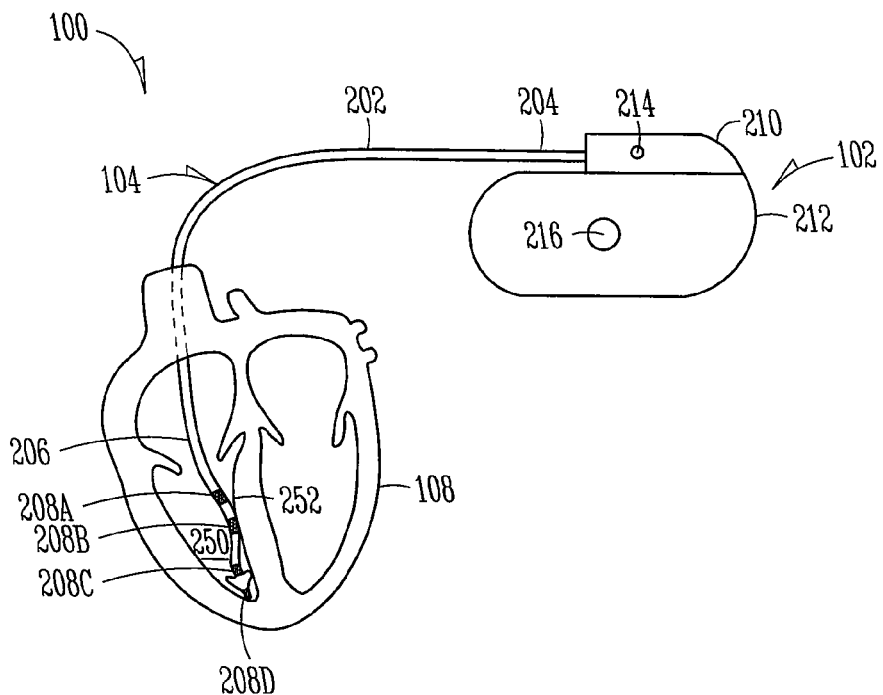
FIG. 2A is a schematic view illustrating an implantable lead system for delivering or receiving signals to and from a heart, as positioned and constructed in accordance with at least one embodiment.
Figure 2B:
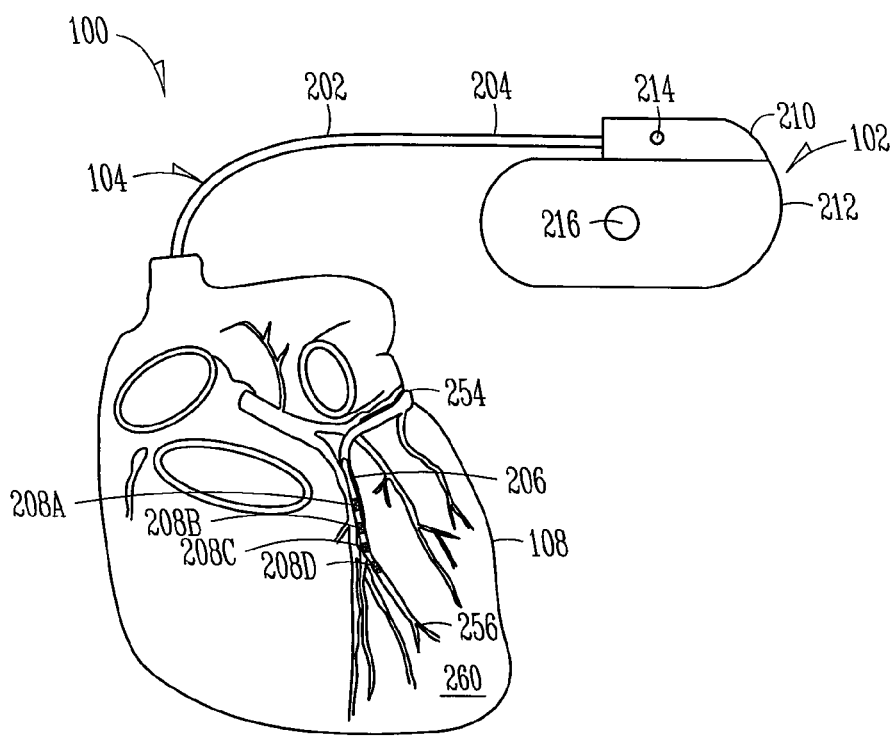
FIG. 2B is a schematic view illustrating an implantable lead system for delivering or receiving signals to and from a heart, as positioned and constructed in accordance with at least one embodiment.

FIGS. 2A-2B are schematic views of a lead system 100 including an IMD 102 and at least one lead 104. Lead 104 includes a lead body 202 which extends from a lead proximal end portion 204, where it is coupled with IMD 102. Lead 104 extends to a lead distal end portion 206, which is coupled with a portion of a heart 108 (e.g., via entanglement, lodging, or helical fixation), when implanted. Lead distal end portion 206 includes at least one electrode 208A, 208B, 208C, 208D that electrically couples lead 104 with heart 108. At least one conductor 602 (cable) or 604 (coil) (both shown in FIG. 6A), electrically couple electrodes 208A, 208B, 208C, 208D with lead proximal end portion 204 and, thus IMD 102. The conductors 602, 604 (FIG. 6A) carry electrical current and pulses or shocks between IMD 102 and electrodes 208A, 208B, 208C, 208D. Lead 104 may be installed using both over-the-wire techniques or non-over-the wire techniques (i.e., stylet driven techniques or catheter delivered techniques).

In the examples shown in FIGS. 2A-2B, lead 104 is a multi-electrode lead that includes a proximal electrode 208A, two intermediate electrodes 208B, 208C, and a distal electrode 208D. Each of the electrodes 208A, 208B, 208C, 208D may be ring electrodes or multi-filar shock coil electrodes and are independently electrically connected to a separate corresponding electrically conductive terminal within a header 210 of IMD 102. Header 210 is affixed to a hermetically sealed housing 212, which may be formed from a conductive metal such as titanium, and which carries, at least portions of, the electronic circuitry of IMD 102. In this example, header 210 includes a header electrode 214 and housing 212 includes a housing electrode 216, both of which may be used in one or more electrode configurations for sensing or stimulating heart 108 as further described in Hansen, et al., U.S. patent application titled "MULTI-SITE LEAD/SYSTEM USING A MULTI-POLE CONNECTION AND METHODS THEREFOR," Ser. No. 11/230,989, filed Sep. 20, 2005.

As shown in FIG. 2A, lead distal end portion 206 of lead 104 is disposed in a right ventricle 250 of heart 108. FIG. 2A further illustrates that lead 104 may include at least one preformed biased portion to urge one or more electrodes thereon against a septal wall 252 for pacing or sensing of the same. Referring now to FIG. 2B, lead distal end portion 206 is disposed in a coronary vein 256 after being guided through a coronary sinus ostium and a coronary sinus 254. Placing lead 104 in a coronary branch vein (e.g., 256) on a left ventricle 260 has been found to be a suitable means for delivering stimulation therapy to a subject suffering from congestive heart failure without having to position lead 104 within left ventricle 260. Other lead 104 placements besides those illustrated in FIGS. 2A-2B are also possible without departing from the scope of the present leads and methods.

Figure 3:
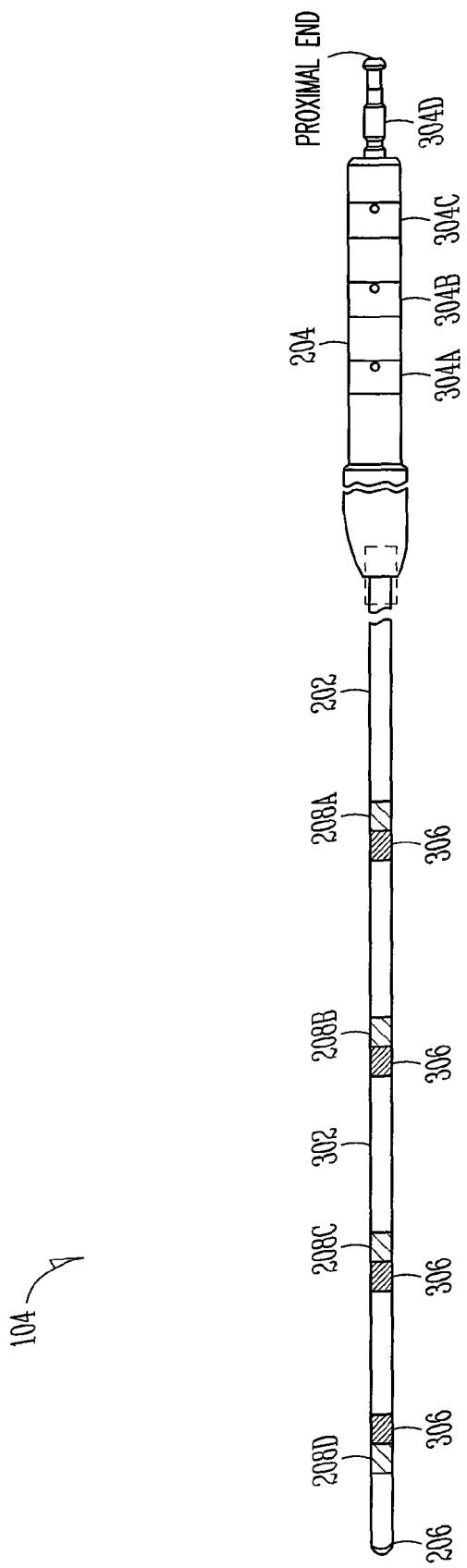
FIG. 3 is a plan view of an implantable lead, as constructed in accordance with at least one embodiment.

FIG. 3 illustrates a plan view of an implantable lead 104. As shown, lead 104 includes a lead body 202 extending from a lead proximal end portion 204 to a lead distal end portion 206 and having an intermediate portion 302 therebetween. In one example, lead body 202 comprises biocompatible tubing such as medical grade polyurethane. In another example, lead body 202 comprises medical grade silicone rubber or other thermoplastic or polymer known in the art to be suitable for use in leads. As discussed above in association with FIG. 1, a lead system 100 includes, among other things, lead 104 for electrically coupling an IMD 102 (FIG. 1) to bodily tissue, such as a heart 108 (FIG. 1), which is to be excited (i.e., stimulated) or sensed by one or more electrodes 208A, 208B, 208C, 208D. It should also be understood that the lead 104 may also include means for sensing other physiological parameters, such as pressure, oxygen saturation, temperature, or the like. Lead 104 may include electrodes 208A, 208B, 208C, 208D only, other physiologic sensors, drug collars 306, or a combination thereof.

Figure 6A:
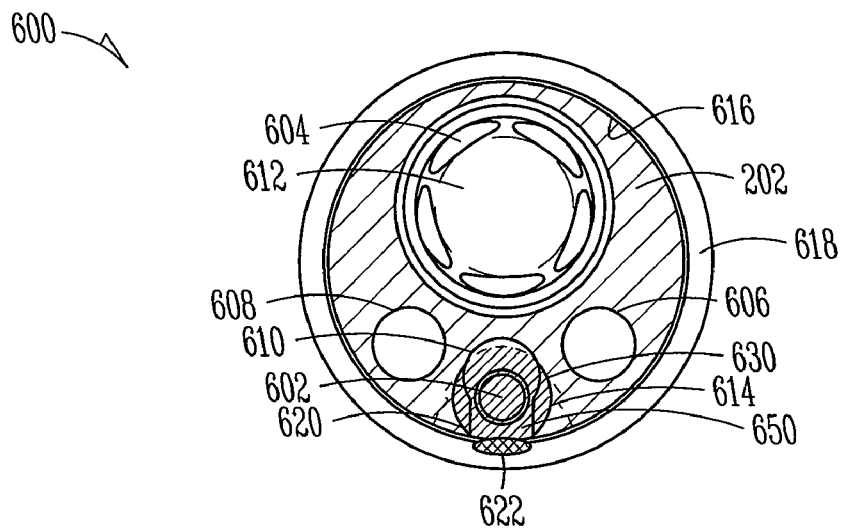
FIG. 6A is a cross-sectional view of an implantable lead taken along line 6A-6A of FIG. 5, as constructed in accordance with at least one embodiment.

In the example shown in FIG. 3, lead proximal end portion 204 includes four terminal connections 304A, 304B, 304C, 304D disposed therealong. Similarly, lead intermediate portion 302 or lead distal end portion 206 include four electrodes 208A, 208B, 208C, 208D disposed therealong. Electrodes 208A, 208B, 208C, 208D are each adapted to sense or stimulate heart 108 (FIG. 1) and are electrically coupled to terminal connections 304A, 304B, 304C, 304D via at least four conductors 602 (cable) or 604 (coil) (both shown in FIG. 6A) contained within lead body 202, such as in one or more internal longitudinally extending lumens 606, 608, 610, 612 (FIG. 6A). Lead proximal end portion 204 and terminal connections 304A, 304B, 304C, 304D disposed therealong are sized and shaped to couple to a multi-pole connector cavity, which may be incorporated into a header 210 (FIGS. 2A-2B) of IMD 102 (FIGS. 2A-2B). It is through the coupling between lead proximal end portion 204 and the multi-polar connector cavity that electrodes 208A, 208B, 208C, 208D are electrically coupled to electronic circuitry of IMD 102.

Advantageously, the present leads and methods provide for secure electrical and mechanical connection between conductors 602 (cable) or 604 (coil) (both shown in FIG. 6A) and electrodes 208A, 208B, 208C, 208D while maintaining a small lead body 202 sized (i.e., diameter), such as sub-5 French. In one example, as discussed in greater detail in association with FIGS. 6A and 6B, lead 104 includes a conductor/electrode connection design using the compressive nature of lead body 202 in conjunction with an appropriately sized electrically conductive interposer (e.g., electrically conductive tube) 614 (FIG. 6A) or similar element. In another example, as discussed in greater detail in association with FIGS. 7A-8B, lead 104 includes a conductor/electrode connection design using a ring member 706 in conjunction with a securing member 702 (FIG. 7A) deformable using, for example, crimping, swaging, welding, or brazing techniques. In yet another example, as discussed in greater detail in association with FIG. 9, lead 104 includes a conductor/conductor connection design using an electrically conductive connector 902 (FIG. 9) couplable with a first conductor on a first end and couplable with a second conductor on a second end. In a further example, as discussed in greater detail in association with FIGS. 10A and 10B, lead 104 includes an axial support member 1002 to reinforce a connection between a distal electrode 208D and (a portion of) lead body 202.

Figure 4:
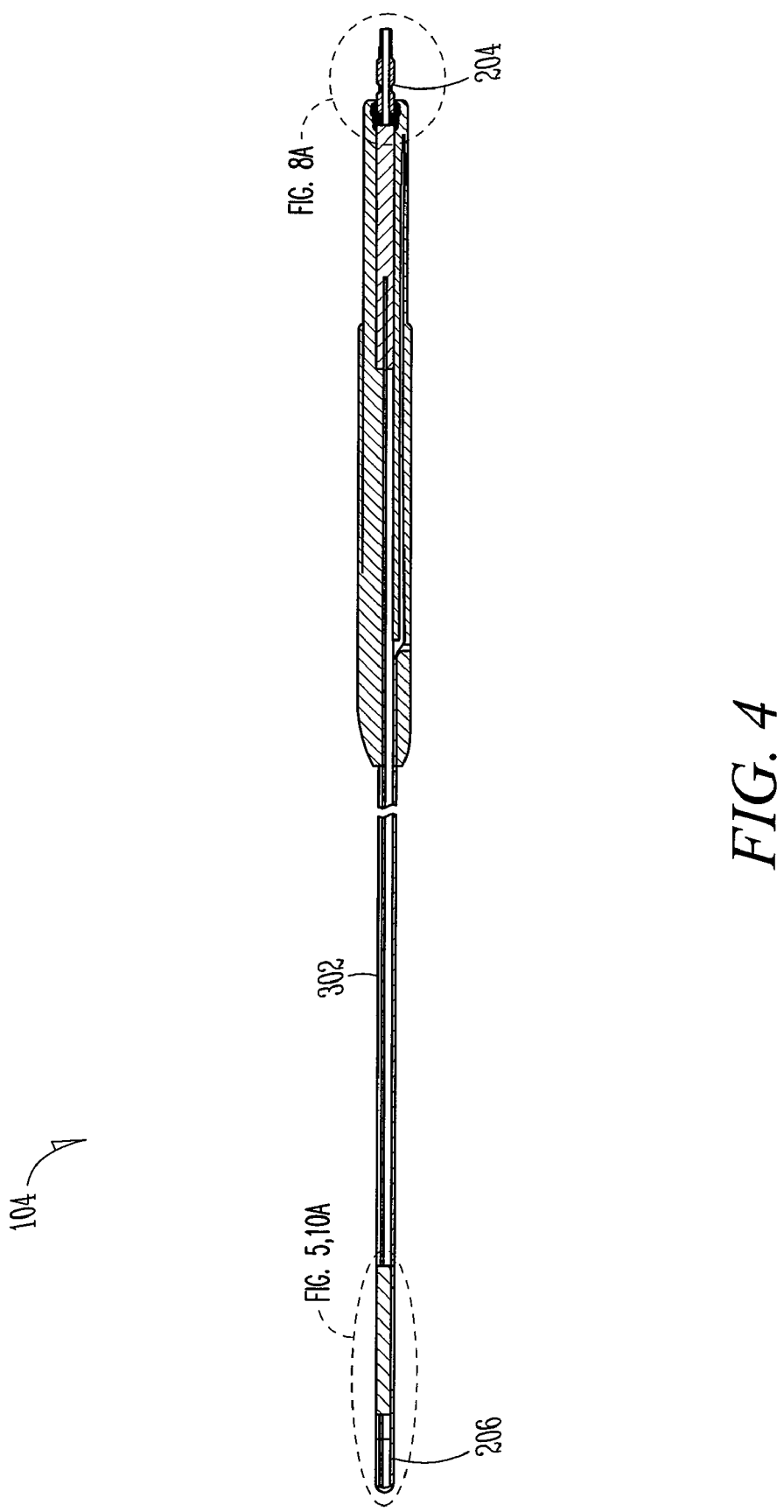
FIG. 4 is a cross-sectional view illustrating an implantable lead, as constructed in accordance with at least one embodiment.
Figure 5:
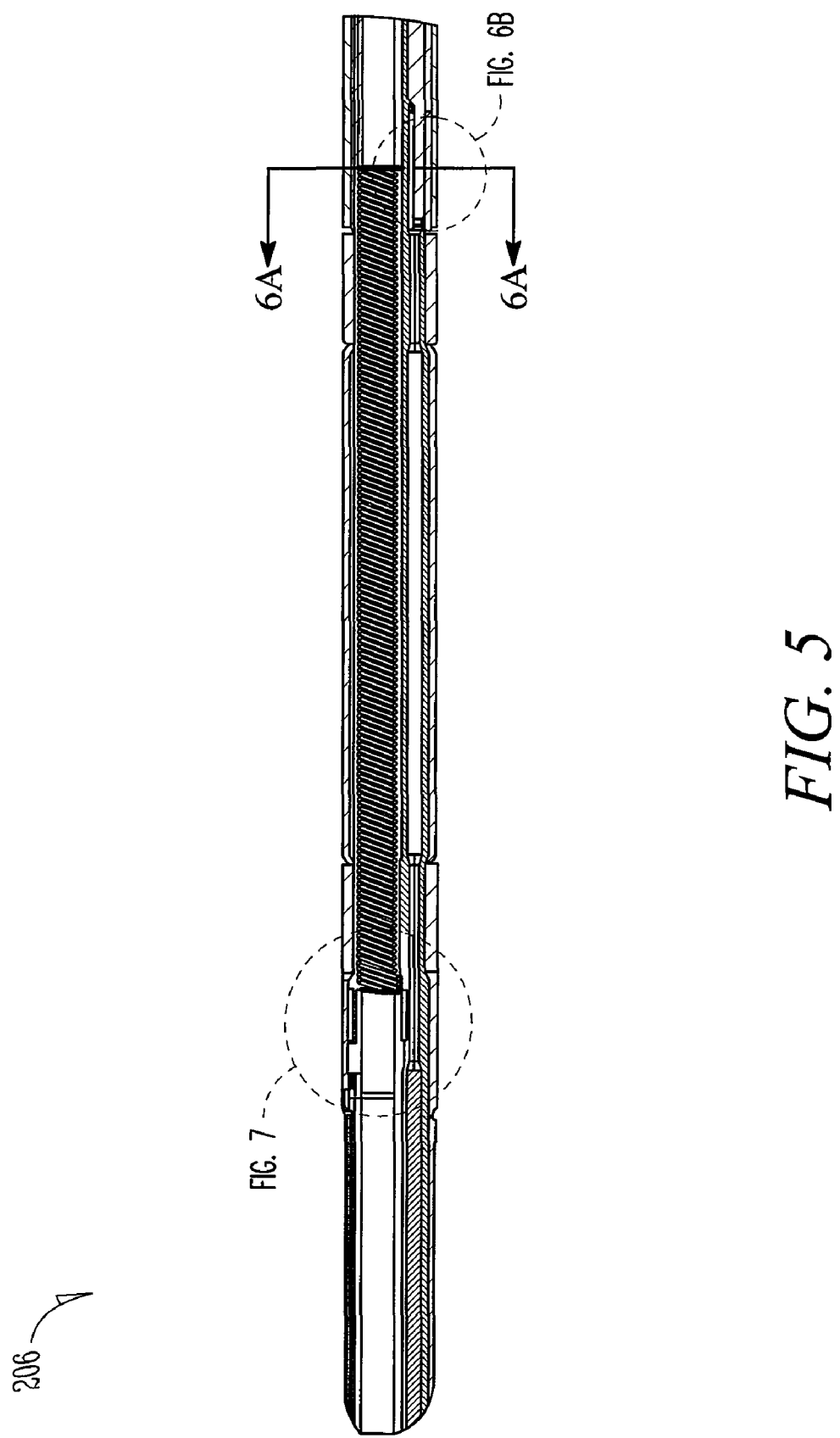
FIG. 5 is a cross-sectional view illustrating a portion of an implantable lead, as constructed in accordance with at least one embodiment.
Figure 8A:
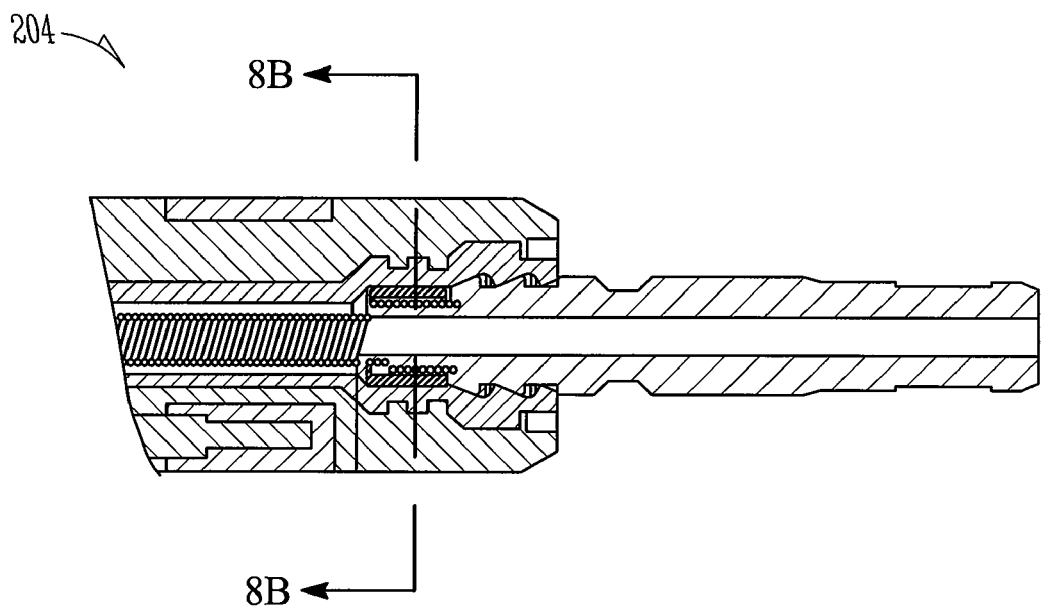
FIG. 8A is a cross-sectional view illustrating a portion of an implantable lead, as constructed in accordance with at least one embodiment.
Figure 10A:
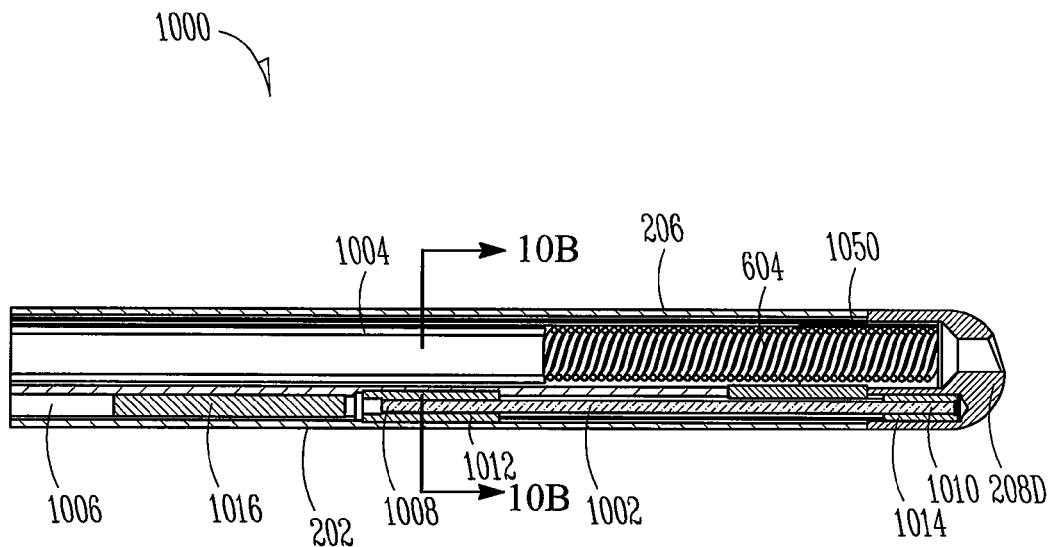
FIG. 10A is a cross-sectional view illustrating a portion of an implantable lead, as constructed in accordance with at least one embodiment.

FIGS. 4, 5, 8A, and 10A illustrate cross-sectional views of an implantable lead 104 or portions thereof. Specifically, FIG. 4 illustrates a cross-sectional view of an implantable lead 104 extending from a lead proximal end portion 204 to a lead distal end portion 206 and having a lead intermediate portion 302 therebetween. FIG. 5 is a cross-sectional view illustrating a lead distal end portion 206 or a lead intermediate portion 302 of an implantable lead 104 (FIG. 4) in greater detail. FIG. 8A is a cross-section view illustrating a lead proximal end portion 204 of an implantable lead 104 (FIG. 4) in greater detail. FIG. 10A is a cross-sectional view illustrating a lead distal end portion 206 or a lead intermediate portion 302 of an implantable lead 104 (FIG. 4) in greater detail.

FIG. 6A illustrates a cross-sectional view taken along line 6A-6A of FIG. 5 of an implantable lead 104 (FIG. 4). FIG. 6A shows, among other things, a conductor/electrode connection design 600 using the compressive nature of a lead body 202 in conjunction with an appropriately sized (i.e., slightly larger than a size of a receiving lumen 610) electrically conductive interposer (e.g., electrically conductive tube) 614, and further in conjunction with an interposer exposing hole or slit (collectively termed "aperture") 650 in a wall of lumen 610. In this example, lead body 202 includes four internal longitudinally extending lumens 606, 608, 610, 612 that allow one or more conductors 602 (cable), 604 (coil) to be received in, and extend along, lead 104 (FIG. 4). In one example, wall portions of at least one lumen (e.g., 610) are sized and shaped to urge an electrically conductive interposer 614 toward an inner surface 616 of a tubular electrode 618 co-axial with, and overlying portions of, lead body 202 through hole or slit 650. When the (slightly larger than lumen 610) electrically conductive interposer 614 is inserted into lumen 610, the wall portions of the lumen deform into an urging shape, such as that depicted by phantom line 630.

In this example, electrically conductive interposer 614 is a metal tube that is coupled with conductor 602 and inserted into the at least one lumen (e.g., 610) having an urging size and shape. The coupling between electrically conductive interposer 614 and conductor 602 may be performed by, among other techniques, crimping, swaging, welding, or brazing. In one such example, as shown in FIG. 6C, electrically conductive interposer 614 is crimped to conductor 602 (FIG. 6B) such that an outer surface 620 of tube 614 mates, in part, with an inner surface 616 of tubular electrode 618 (FIG. 6B) (i.e., $R_1$, representing a radius from a lead body 202 center to outer surface 620, is approximately equal to $R_2$, representing a radius from the lead body 202 center to inner surface 616). This ensures intimate contact and an adequate fitting for welding 622 tubular electrode 618 to electrically conductive interposer 614. After being inserted in lumen 610 and urged toward inner surface 616 of tubular electrode 618 (by wall portions of lumen 610) through hole or slit 650, electrically conductive interposer 614 may be coupled to tubular electrode 618, such as by spot or laser welding 622 (see also FIG. 6B), brazing, or using a conductive adhesive.

Figure 6B:
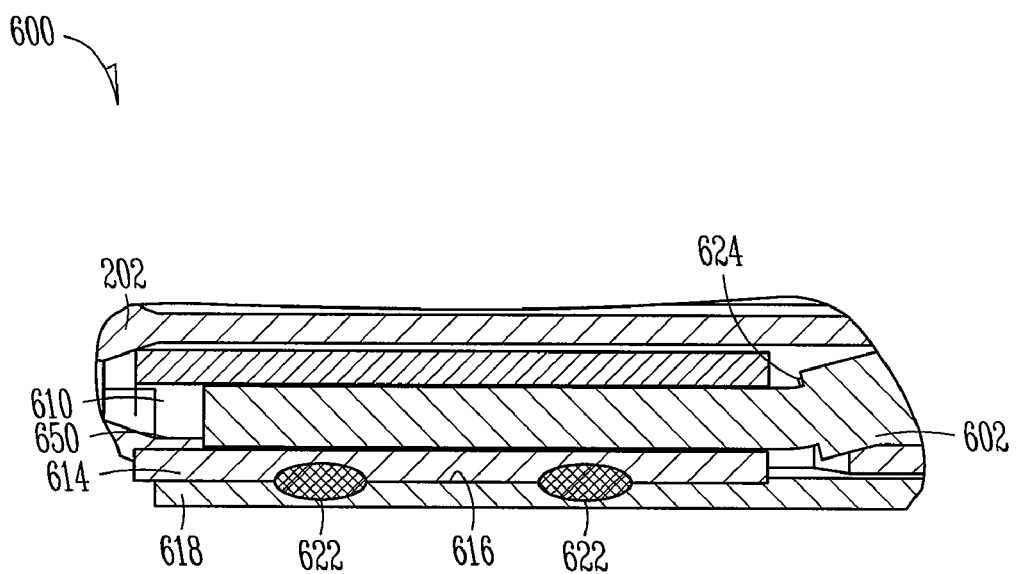
FIG. 6B is a cross-sectional view illustrating a portion of an implantable lead, as constructed in accordance with at least one embodiment.
Figure 6C:
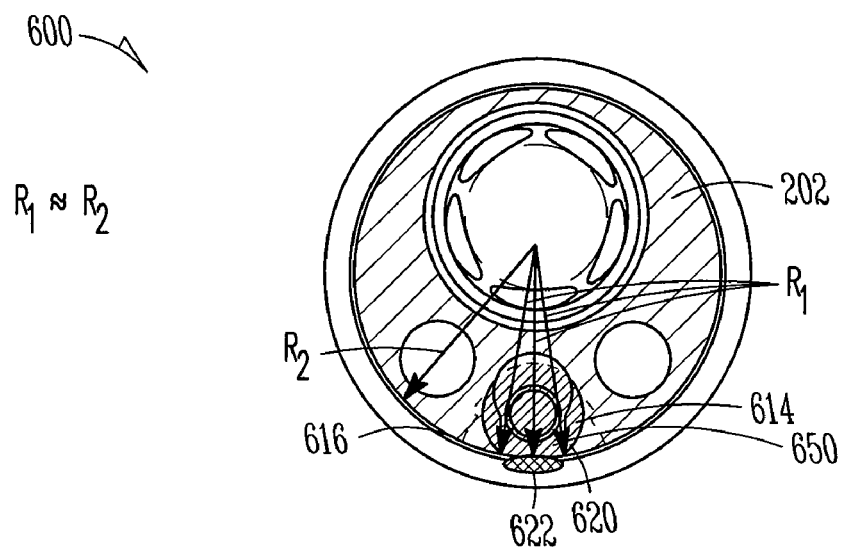
FIG. 6C is a cross-sectional view of an implantable lead taken along line 6A-6A of FIG. 5, as constructed in accordance with at least one embodiment.

FIG. 6B is a cross-sectional view illustrating a lead distal end portion 206 or a lead intermediate portion 302 of an implantable lead 104. Specifically, FIG. 6B illustrates one or more spot or laser welding 622 that may be made between an electrically conductive interposer 614 and a tubular electrode 618, in accordance with at least one embodiment of a conductor/electrode connection design 600. As shown in FIG. 6B, wall portions of a lumen 610 in lead body 202 are sized and shaped to urge electrically conductive interposer 614 toward an inner surface 616 of tubular electrode 618 through hole or slit 650. As also shown, electrically conductive interposer 614 is coupled with a conductor 602, such as by crimping, swaging, welding, or brazing. Prior to the crimping, swaging, welding, or brazing, most of the insulating coating 624 on a distal end of conductor 602 may need to be removed to allow for electrical communication between electrically conductive interposer 614 and conductor 602. Although not shown in FIG. 6B, weld 622 may be a continuous weld between interposer 614 and electrode 618.

Figure 6D:
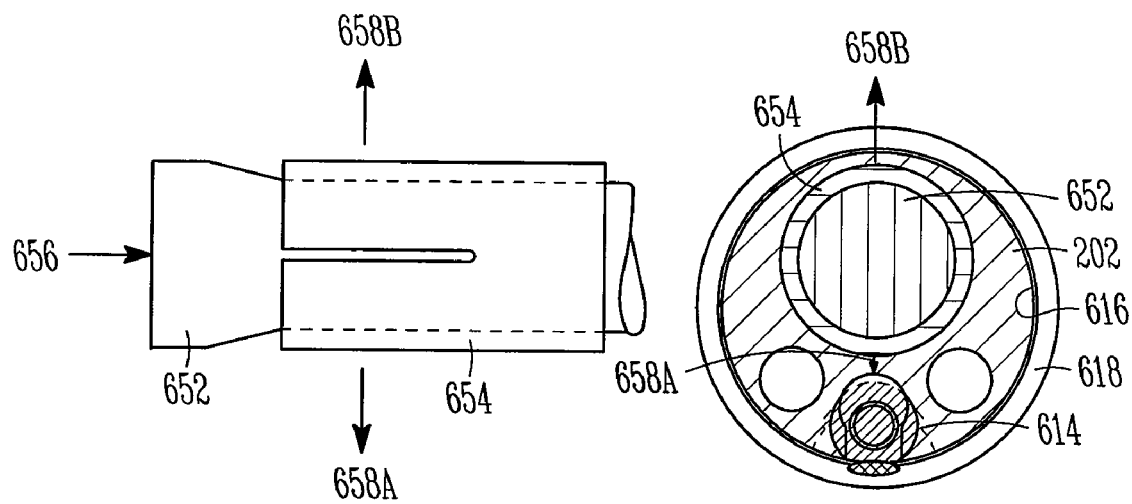
FIG. 6D is a cross-sectional view of an implantable lead including an urging member taken along line 6A-6A of FIG. 5, as constructed in accordance with at least one embodiment.

FIG. 6D illustrates a removable expanding mandrel 652 surrounded by a split cylinder 654, both of which may be inserted into (coil receiving) lumen 612 (FIG. 6A) of lead body 202 to urge electrically conductive interposer 614 toward inner surface 616 of tubular electrode 618. In one example, movement of mandrel 652 in direction 656 causes split cylinder 654 to expand in directions 658A, 658B, which in turn urges lead body 202 against interposer 614 in a direction toward electrode 618.

Figure 7A:
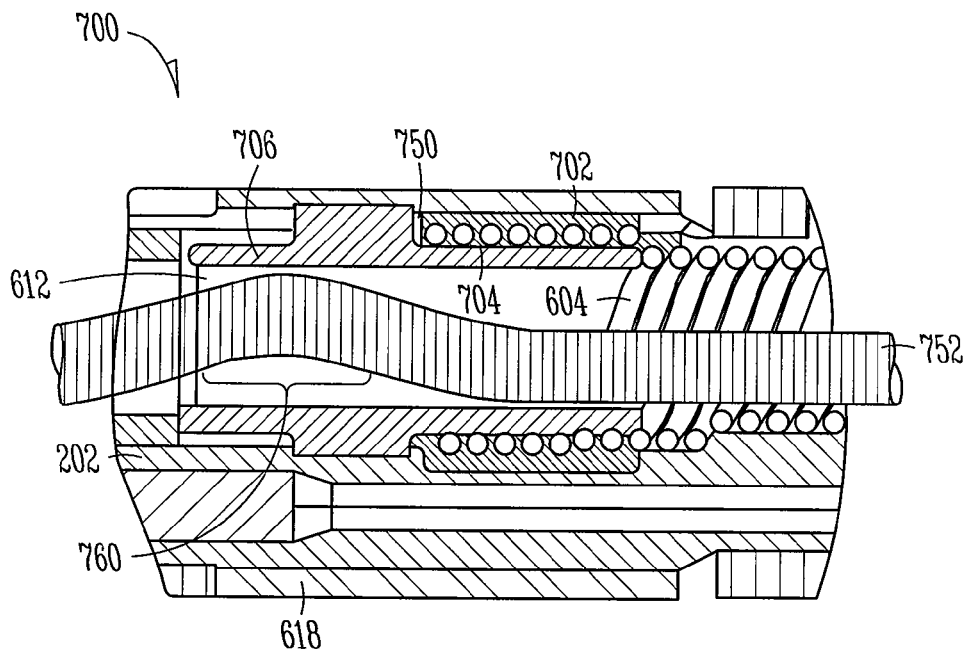
FIG. 7A is a cross-sectional view illustrating a portion of an implantable lead and an urging member, as constructed in accordance with at least one embodiment.
Figure 7B:
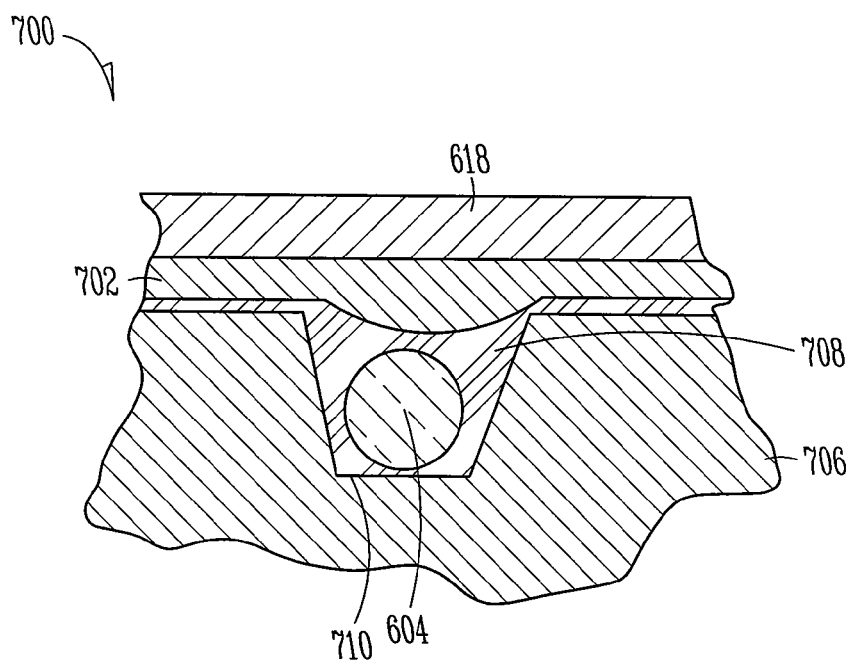
FIG. 7B is a cross-sectional view illustrating a portion of an implantable lead, as constructed in accordance with at least one embodiment.

FIGS. 7A and 7B illustrate a cross-sectional view of a lead distal end portion 206 (FIG. 5) or a lead intermediate portion 302 of an implantable lead 104 (FIG. 4). FIGS. 7A and 7B show, among other things, a conductor/electrode connection design 700 using a ring member 706.

In the example of FIG. 7A, a lead body 202 includes at least one internal longitudinally extending lumen 612 that allows one or more conductors 604, such as a coil conductor, to be received in, and extend along, lead 104 (FIG. 4). In one example, a distal end portion of conductor 604 extends along lead 104 (FIG. 4) to a location adjacent to an outer surface 704 of ring member 706, which is disposed within lumen 612, and coupled thereto. As shown, a portion of ring member 706 extends through a hole or slit 750 in a wall of lumen 612.

The distal end portion of conductor 604 may be coupled to ring member 706 using one or more of a variety of techniques. In one example, conductor 604 is coupled to ring member 706 by first urging conductor 604 over a slightly larger diameter ring member 706. In another example, a securing member 702 is disposed around the distal portion of conductor 604 and ring member 706 and deformed, such as by crimping, (rotary) swaging, welding, or brazing. Rotary swaging is a metal forming process for the diametrical reduction of annular securing members, such as bars, tubes, wires, etc. In this example, securing member 702 is deformed over the distal end portion of conductor 604 thereby coupling the conductor 604 to ring member 706. As shown in FIG. 7A, a tubular electrode 618 co-axial with, and overlying portions of, lead body 202 is electrically coupled with conductor 604 via (conductive) securing member 702 and/or (conductive) ring member 706. In one example, a removable preformed mandrel 752 is used to urge ring member 706 toward electrode 618 prior to coupling between the same. As shown, mandrel 752 includes a preformed bend 760 to urge ring member 706 toward electrode 618.

In the example of FIG. 7B, an adhesive 708 and one or more grooves (or threads) 710 are used in conjunction with a securing member 702 to couple a conductor 604 to a ring member 706. As discussed above, after securing member 702 is positioned over a distal end portion of conductor 604 and ring member 706, securing member 702 may then deformed to snugly secure conductor 604 to ring member 706. The deformation decreases the internal diameter of securing member 702 thereby reconfiguring a shape of securing member 702 and pinching adhesive 708 (which may be inserted for additional coupling strength) over conductor 604 and into the one or more grooves (or threads) 710 in ring member 706. Grooves (or threads) 710 may be used to provide additional axial strength at the conductor/electrode connection design

700. Adhesive 708 may be a suitable medical grade adhesive, such as silicone based adhesive, a two-part adhesive, a conductive adhesive, or another similar adhesive. Adhesive 708 forms a secure mechanical bond between securing member 702, conductor 604, and ring member 710. As shown in FIG. 7B, a tubular electrode 618 co-axial with, and overlying portions of, lead body 202 is electrically coupled with conductor 604 via (conductive) securing member 702 and/or (conductive) ring member 706.

Figure 8B:
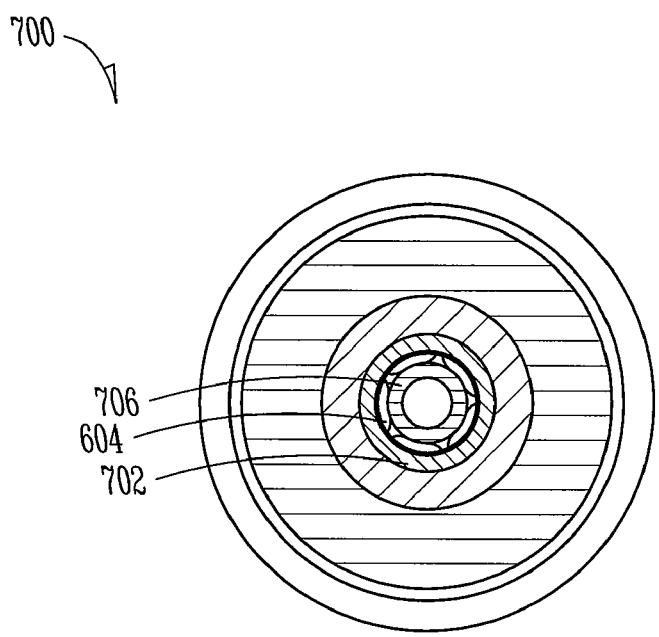
FIG. 8B is a cross-sectional view of an implantable lead taken along line 8B-8B of FIG. 8A, as constructed in accordance with at least one embodiment.

FIG. 8B is a cross-sectional view of an implantable lead 104 (FIG. 4) taken along line 8B-8B of FIG. 8A. FIG. 8B shows a conductor/electrode connection design 700 using a securing member 702 deformable using, for example, rotary swaging. In this example, securing member 702 is deformed over a conductor 604 to couple conductor 604 to a ring member 706.

Figure 9:
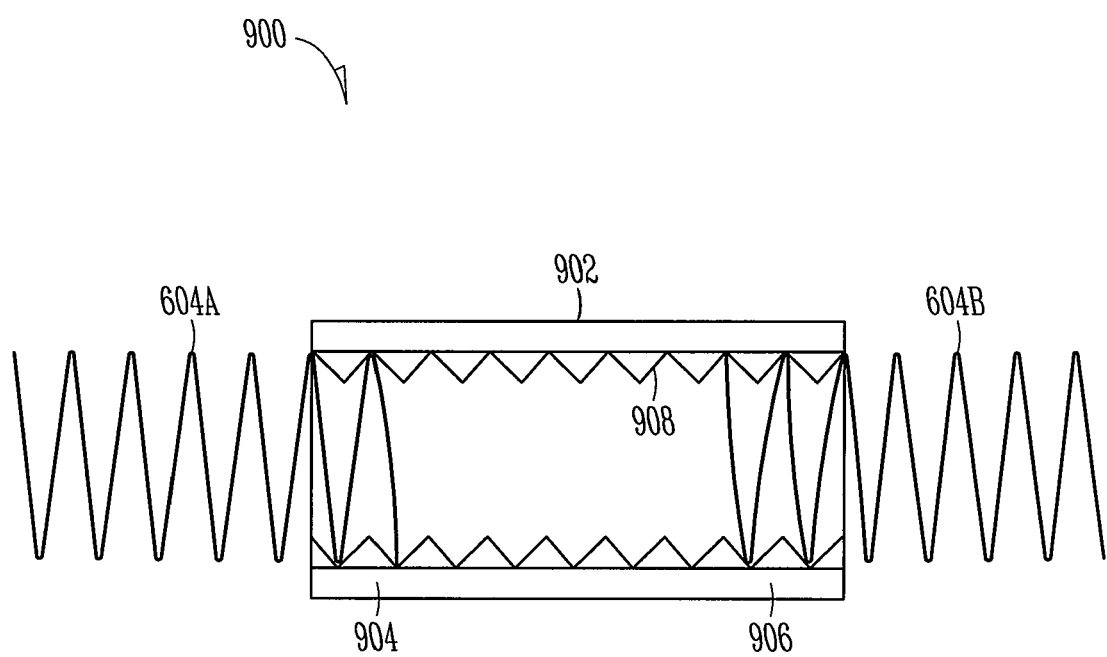
FIG. 9 is a schematic view illustrating an electrically conductive connector, as constructed in accordance with at least one embodiment.

FIG. 9 illustrates an electrically conductive connector 902 for use in a conductor/conductor connection design 900. Conductor/conductor connection design 900 may be used to advantageously couple a first (coil) conductor 604A to a (coil) second conductor 604B within a lead body 202 (FIG. 3) providing, among other things, different mechanical or electrical properties or cost savings (e.g., a first conductor may be formed from an expensive material and a second, longer conductor may be formed from a less expensive material).

Electrically conductive connector 902 includes a first end portion 904 couplable with first conductor 604A and a second end portion 906 couplable with second conductor 604B. In the example shown, electrically conductive connector 902 includes one or more internal grooves (or threads) 908. In another example, electrically conductive connector 902 includes one or more external grooves (or threads). Conductors 604A, 604B may be further secured (i.e., in addition to the one or more grooves) to electrically conductive connector 902 by rotary swaging, laser or resistance welding, brazing, mechanical swaging, or crimping. In one example, conductors 604A, 604B are further secured to electrically conductive connector using a securing member disposed and deformed around a portion of the conductors by rotary swaging techniques. In examples in which one or both of first conductor 604A or second conductor 604B are coupled via one or more external grooves (such as those associated with screw threads), shrink tubing or a compressive/elastic lead body 202 (FIG. 6A) may be used to further secure such conductors to connector 902.

FIG. 10A illustrates a cross-sectional view of a lead distal end portion 206 of an implantable lead 104 (FIG. 4). FIG. 10A shows, among other things, a reinforcement design 1000 for increasing the axial strength between a distal electrode (e.g., 208D) and a lead body 202. In this example, lead body 202 includes at least a first 1004 and second 1006 internal longitudinally extending lumens. A conductor 604 is received in, and extends along, first lumen 1004 and electrically couples to distal electrode 208D at a distal end thereof.

To provide additional axial strength to the distal electrode 208D/conductor 604 connection joint, lead 104 (FIG. 4) may include an axial support member 1002 received in the second lumen 1006. Axial support member 1002 extends from an axial support member proximal end portion 1008 to an axial support member distal end portion 1010. As shown, axial support member proximal end portion 1008 is coupled with a first retaining member 1012, while axial support member distal end portion 1010 is coupled with a second retaining member 1014. Retaining members 1012, 1014 are engaged with lead body 202 and distal electrode 208D, respectively, thereby providing the additional axial support to the distal electrode/conductor joint.

Many options are possible for reinforcement design 1000. In one example, axial support member 1002 is a cable. In another example, first 1012 and second 1014 retaining members include at least one of a crimped tube, a swaged tube, a welded tube, or a brazed tube (i.e., a couplable tube). In one such example, distal electrode 208D is placed over an outer surface of the crimped or swaged tube and laser welded thereto. In another example, an outer diameter of first retaining member 1012 is greater than a diameter of second lumen 1006 (see FIG. 10B). To make room for such larger retaining member 1012, lumen 1006 is cut or ablated in the placement vicinity of member 1012. In such an example, distal electrode 208D is held in place because first retaining member cannot slide through second lumen 1006 due to its larger size. In addition, lead body 202 may be fused around retaining member 1012 to provide further retainment strength. In yet another example, a plug member 1016 (e.g., a polyurethane filament) or other sealant means is inserted in second lumen 1006 proximal to first retaining member 1012 and adhered to lead body 202 (e.g., by heat fusing techniques) to electrically isolate reinforcement member 1012 and electrode 208D from a more proximal conductor in a second lumen. In further examples, an outer surface of distal electrode 208D is isodiametric or non-isodiametric with an outer surface of lead body 202, or one or more knots are used in conjunction with one or both of the first and the second retaining members.

Figure 10B:
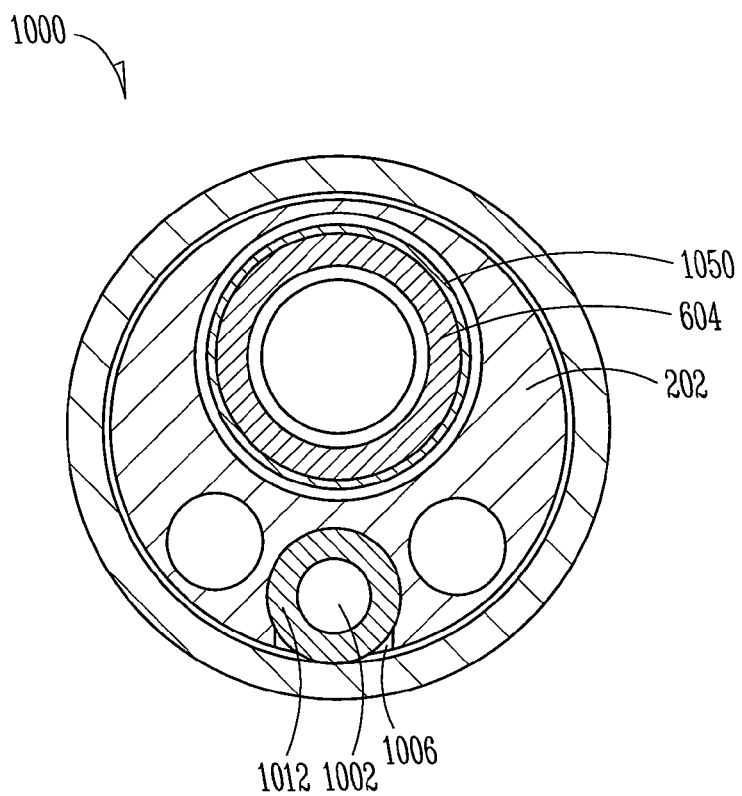
FIG. 10B is a cross-section view of an implantable lead taken along line 10B-10B of FIG. 10A, as constructed in accordance with at least one embodiment.

FIG. 10B is a cross-sectional view of an implantable lead 104 (FIG. 4) taken along line 10B-10B of FIG. 10A. FIG. 10B shows, among other things, an outer diameter of first retaining member 1012 greater than a diameter of second lumen 1006 of lead body 202 and covered by fusing of the same thereby precluding retaining member 1012 from being pulled through lumen 1006 without high force. As discussed above, axial supporting member 1002 is coupled with first retaining member 1012 on axial supporting member proximal end 1008 and coupled with second retaining member 1014 (FIG. 10A) on axial supporting member distal end 1010. As further discussed above, distal electrode 208D may be laser welded (or otherwise secured) to second retaining member 1014 (FIG. 10A). Accordingly, axial load placed on distal electrode 208D is supported, at least in part, by reinforcement design 1000. As also shown in FIG. 10B, a weld ring 1050 coupled to conductor 604 on an inner surface and fused to lead body 202 on an outer surface may also be used to provide axial support to distal electrode 208D/conductor 604 connection joint.

Figure 11:
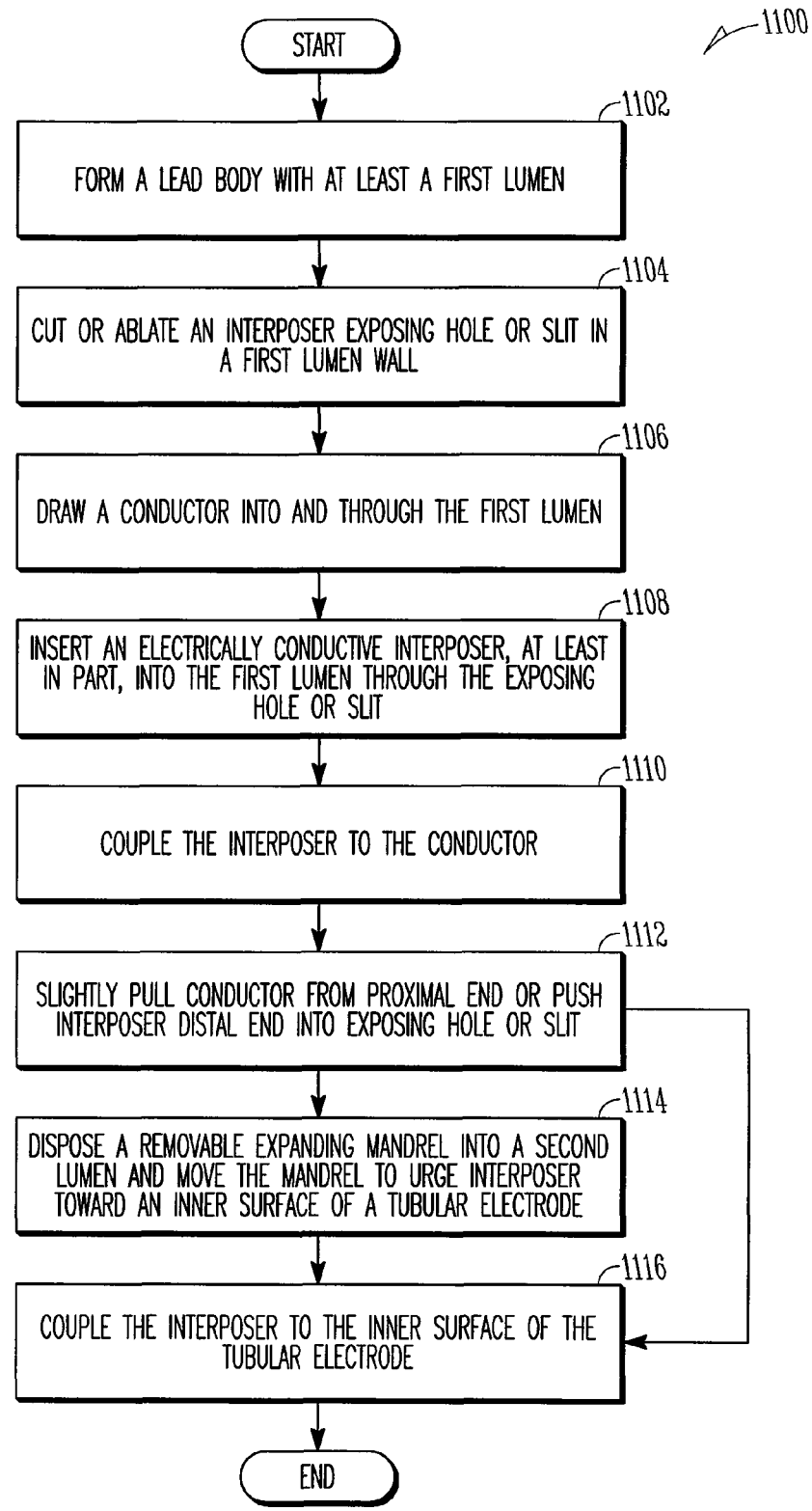
FIG. 11 is a flow diagram illustrating a method of manufacturing an implantable lead, as constructed in accordance with at least one embodiment.

FIG. 11 is a flow diagram illustrating a method 1100 of manufacturing an implantable lead. At 1102, a lead body extending form a lead proximal end to a lead distal end is formed. Forming the lead body includes forming at least a first longitudinally extending lumen therein. In varying examples, wall portions of the first lumen are sized and shaped to urge an appropriately (larger) sized element (e.g., an electrically conductive interposer—see 1108) placed in the first lumen outward toward a tubular electrode co-axial with, and overlying portions of, the lead body. At 1104, an interposer exposing hole or slit is cut or ablated in a first lumen wall (opposite the urging wall portions) to receive the interposer and allow such element to electrically couple a conductor (see 1106) and the tubular electrode. At 1106, the conductor is drawn into and through the first lumen At 1108, the electrically conductive interposer is inserted into the first lumen such that the conductor is located therewithin (i.e., the (tubular) interposer is slid onto at least a portion of the conductor). At 1110, the electrically conductive interposer is coupled to the conductor. This may initially include, among other things, removing an insulative coating on an outer side of the conductor. In one example, the electrically conductive interposer is coupled to the conductor via crimping, swaging, welding, or brazing. In one such example, the electrically conductive interposer is crimped to the conductor such that an outer surface of the electrically conductive interposer mates with (a sized and shape of) an inner surface of the tubular electrode, thereby providing a more conducive juncture for the process of 1112.

At 1112, the conductor is slightly pulled from a conductor proximal end or an interposer distal end is pushed into the exposing hole or slit so that the interposer is fully within the outer boundaries of the lead body. Optionally, at 1114, a removable expanding mandrel may be disposed into a second lumen to urge the interposer outward toward the inner surface of the tubular electrode. At 1116, the interposer is coupled to the inner surface of the tubular electrode via welding, brazing, conductive adhesives, or other suitable techniques.

FIG. 12 is a flow diagram illustrating another method 1200 of manufacturing an implantable lead. At 1202, a lead body extending from a lead proximal end portion to a lead distal end portion and including an internal longitudinally extending lumen is formed. At 1204, a hole or slit in a lumen wall is cut or ablated. At 1206, a ring member is disposed within the lumen such that a portion of the ring member is inserted through the hole or slit in the lumen wall. At 1208, a conductor is drawn into and through the lumen such that a distal end portion of the conductor is adjacent the ring member.

The conductor may be coupled to the ring member using a variety of techniques (see, e.g., 1210, 1216, and 1218). A first technique includes a securing member being disposed around the distal end portion of the conductor and the ring member (at 1210). Optionally, at 1212, one or more grooves or threads may be formed on the ring member. At 1214, the securing member is deformed over the conductor for coupling purposes. In one such example, portions of the securing member are pushed into or over the one or more grooves or threads. A second technique includes using a conductive adhesive to couple the conductor to the ring member (at 1216). A third coupling technique includes forming one or more grooves or threads on the ring member (at 1218) and urging the conductor onto the one or more grooves or threads (at 1220). Such urging may come by way of the compressive nature of the lead body or a removable preformed mandrel. In addition, the conductor may be coupled to the ring member using only urging forces, such as the compressive nature of the lead body or through the use of the removable preformed mandrel.

At 1222, a tubular electrode co-axial with the lead body is overlaid on portions thereof. In one example, the lead body is overlaid on portions of the lead body such that a substantially smooth, uninterrupted surface at the interface of the tubular electrode and an outer surface of the lead body results. A smooth outer lead body surface may be desirable as it allows for easy passage of the lead through veins of a subject and further minimizes thrombus formation and the like.

Using various techniques, the tubular electrode is electrically coupled with the conductor. In one example, the tubular electrode is coupled with a portion of the ring member, which (as discussed above) may be electrically coupled to the conductor. Such coupling may include one or more of welding (at 1224), brazing (at 1224), or using a conductive adhesive (at 1226). Portions of the ring member may be urged toward an inner surface of the tubular electrode using, for example, the preformed mandrel at 1228 or another urging means.

The leads and methods described herein provide numerous advantages over conventional lead designs including secure electrical and mechanical connection between a conductor, such as a small multi-strand conductor cable, and an electrode (e.g., a ring electrode or a multi-filar shock coil electrode). In addition, the leads and methods provide axial reinforcement between a distal electrode and a lead body. Furthermore, the leads and methods allow for the creation of a smaller-sized lead (e.g., sub-5 French), which advantageously provides for easier and deeper lead delivery and lower sensing/stimulating thresholds. In one such example, the present leads and methods provide a small-sized lead with multiple conductors and electrodes.

Several other advantages are also made possible by the present leads and methods. As one example, the leads and methods reduce or eliminate the reliance on adhesives to couple a conductor to an electrode. Advantageously, by reducing or eliminating reliance on adhesives, manufacturing efficiency can be increased (e.g., don't need to wait for adhesives to cure), and conductor/electrode joint failure caused by adhesive bond strength decreasing over time (e.g., due to reactions with bodily fluids or improper adhesive preparation) can be reduced or eliminated.

It is to be understood that the above description is intended to be illustrative, and not restrictive. It should be noted that the above text discusses, among other things, interconnections of implantable lead conductors and electrodes for use in cardiac situations; however, the present leads and methods are not so limited. Many other embodiments and contexts, such as for non-cardiac nerve and muscle situations, will be apparent to those of skill in the art upon reviewing the above description. The scope should, therefore, be determined with reference to the appended claims, along with the full scope of equivalents to which such claims are entitled.

What is claimed is:

1. An implantable lead comprising:
   a lead body extending from a lead proximal end portion to a lead distal end portion and having a lead intermediate portion therebetween, the lead body including a longitudinally extending internal lumen;
   a conductive linking member having a base and a projection laterally extending from the base, the base disposed at least partially within the lumen and the projection partially extending through an aperture in a lumen wall;
   a conductor received in and extending along the lumen, a portion of the conductor disposed adjacent to the base of the linking member and electrically coupled thereto; and
   a tubular electrode co-axial with and overlying portions of the lead body, the tubular electrode electrically coupled with the conductor, in part, via the projection of the linking member extending through the lumen wall.

2. The implantable lead of claim 1, wherein the base of the linking member includes an annular, ring-like shape.

3. The implantable lead of claim 2, wherein the projection extends at least contralaterally from an outer surface of the annular, ring-like shape of the linking member.

4. The implantable lead of claim 1, further comprising a securing member disposed around the base of the linking member and the portion of the conductor disposed adjacent the base, the securing member deformably coupled around the conductor firmly attaching the conductor to the linking member.

5. The implantable lead of claim 4, wherein the securing member includes a crimped, swaged, welded, or brazed securing member; and
   wherein deformation of the securing member decreases a radius of curvature of an inner surface of the base.

6. The implantable lead of claim 1, wherein an outer surface of the base of the linking member includes one or more grooves or threads coupled to the adjacent portion of the conductor.

7. The implantable lead of claim 1, further comprising an adhesive disposed between the base of the linking member and the portion of the conductor disposed adjacent the base.

8. The implantable lead of claim 1, wherein a portion of the lumen wall compressively urges the projection of the linking member through the aperture in the lumen wall toward an inner surface of the tubular electrode.

9. The implantable lead of claim 1, wherein the conductor includes a coil conductor having an inner surface and an outer surface, the inner surface of the coil conductor mechanically and electrically coupled to an outer surface of the base of the linking member.

10. The implantable lead of claim 9, wherein a radius of curvature of an outer surface of the base is greater than a radius of curvature of the inner surface of the coil conductor.

11. The implantable lead of claim 1, wherein the portion of the conductor disposed adjacent to the base of the linking member and electrically coupled thereto includes a distal end portion of the conductor.

12. The implantable lead of claim 1, wherein the aperture in a lumen wall includes at least one of a hole or a slit.

13. An implantable lead comprising:
   a lead body extending from a lead proximal end portion to a lead distal end portion and having a lead intermediate portion therebetween, the lead body including a longitudinally extending internal lumen;
   a conductive ring member having a base and a projection extending laterally outward from the base, the projection extending partially through an aperture in a lumen wall;
   a conductor received in and extending along the lumen, a portion of the conductor disposed adjacent to the base of the ring member and electrically coupled thereto; and
   a tubular electrode co-axial with the lead body, the tubular electrode electrically coupled with the conductor via the ring member.

14. The implantable lead of claim 13, wherein an axial length of the base of the ring member is greater than an axial length of the projection extending from the base.

15. The implantable lead of claim 13, wherein the conductor includes a coil conductor; and wherein a diameter of an outer surface of the base is greater than a diameter of an inner surface of the coil conductor.

16. A method of manufacturing an implantable lead, the method comprising:
   forming a lead body extending from a lead proximal end portion to a lead distal end portion and having a lead intermediate portion therebetween, including forming a longitudinally extending lumen within the lead body;
   disposing a base of a conductive linking member within the lumen and inserting a projection of the linking member through an aperture in a lumen wall;
   drawing a conductor into and through the lumen, including disposing a portion of the conductor adjacent to a base of the linking member;
   coupling the conductor to the base; and
   overlying portions of the lead body with a tubular electrode, the tubular electrode co-axial with the lead body and electrically coupled with the conductor.

17. The method of claim 16, wherein coupling the conductor to the base of the linking member includes disposing a securing member around the base and the portion of the conductor disposed adjacent the base; and
   deforming the securing member over the conductor.

18. The method of claim 16, wherein coupling the conductor to the linking member includes coupling an inner surface of a coil conductor to an outer surface of the base using one or more grooves or threads.

19. The method of claim 16, wherein forming the longitudinally extending lumen includes forming a lumen wall portion sized and shaped to urge the projection of the linking member toward an inner surface of the tubular electrode.

20. The method of claim 16, wherein electrically coupling the tubular electrode with the conductor includes using a preformed mandrel to urge the projection of the linking member toward an inner surface of the tubular electrode.

21. The method of claim 16, wherein overlying portions of the lead body with the tubular electrode includes forming a substantially isodiametric surface at an interface of the tubular electrode and an outer surface of the lead body.

22. The method of claim 16, wherein inserting the projection of the linking member through the aperture includes extending the projection laterally beyond an outer diameter of the conductor.

* * * * *